(12) United States Patent
Hart et al.

(10) Patent No.: US 7,837,695 B2
(45) Date of Patent: Nov. 23, 2010

(54) SKIN TREATMENT SYSTEM

(75) Inventors: Jackie Hart, Rocklin, CA (US); James Patrick Murray, Oakland, CA (US)

(73) Assignee: DermaSweep, Inc., Rocklin, CA (US)

( * ) Notice: Subject to any disclaimer, the term of this patent is extended or adjusted under 35 U.S.C. 154(b) by 600 days.

(21) Appl. No.: 11/805,107

(22) Filed: May 22, 2007

(65) Prior Publication Data

US 2008/0215068 A1 Sep. 4, 2008

Related U.S. Application Data

(63) Continuation-in-part of application No. 11/172,698, filed on Jun. 30, 2005.

(51) Int. Cl.
*A61B 17/50* (2006.01)

(52) U.S. Cl. ..................................... 606/131

(58) Field of Classification Search .................. 606/131, 606/132, 133; 604/290, 289, 318–327; 451/38, 451/87, 90
See application file for complete search history.

(56) References Cited

U.S. PATENT DOCUMENTS

| | | |
|---|---|---|
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 4,378,804 A | 4/1983 | Cortese, Jr. |
| 4,646,482 A | 3/1987 | Chitjian |
| 4,957,747 A | 9/1990 | Stiefel |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,100,412 A | 3/1992 | Rosso |
| 5,121,388 A | 6/1992 | Perdikaris et al. |
| 5,207,234 A | 5/1993 | Rosso |
| 5,697,920 A * | 12/1997 | Gibbons ...................... 604/289 |
| 5,800,446 A | 9/1998 | Banuchi |
| 5,810,842 A | 9/1998 | Di Fiore et al. |
| 5,971,999 A | 10/1999 | Naldoni |
| 6,042,552 A | 3/2000 | Cornier |
| 6,241,739 B1 | 6/2001 | Waldron |
| 6,423,078 B1 | 7/2002 | Bays et al. |
| 6,500,183 B1 | 12/2002 | Waldron |
| 6,641,591 B1 | 11/2003 | Shadduck |
| 6,695,583 B2 | 2/2004 | Schmaling et al. |
| 7,070,488 B2 * | 7/2006 | Suissa et al. ................... 451/87 |
| 7,153,311 B2 * | 12/2006 | Chung ......................... 606/131 |
| 7,276,072 B2 * | 10/2007 | Chung ......................... 606/131 |
| 2004/0010268 A1 | 1/2004 | Gabehart |
| 2004/0122447 A1 * | 6/2004 | Harmon et al. ............. 606/131 |
| 2004/0143274 A1 | 7/2004 | Shadduck |

* cited by examiner

*Primary Examiner*—Anhtuan T Nguyen
*Assistant Examiner*—Tuan V Nguyen
(74) *Attorney, Agent, or Firm*—Thomas R. Lampe

(57) ABSTRACT

Apparatus for abrading skin and simultaneously delivering a liquid topical solution to the skin includes a vacuum source, a hand-held applicator wand including a skin abrading brush, and a collection canister for collecting exfoliated skin particles and any liquids associated therewith entrained by an air flow between the hand-held applicator wand and the collection canister. The vacuum source also creates a flow from a container containing the liquid topical solution to the skin abrading brush.

3 Claims, 3 Drawing Sheets

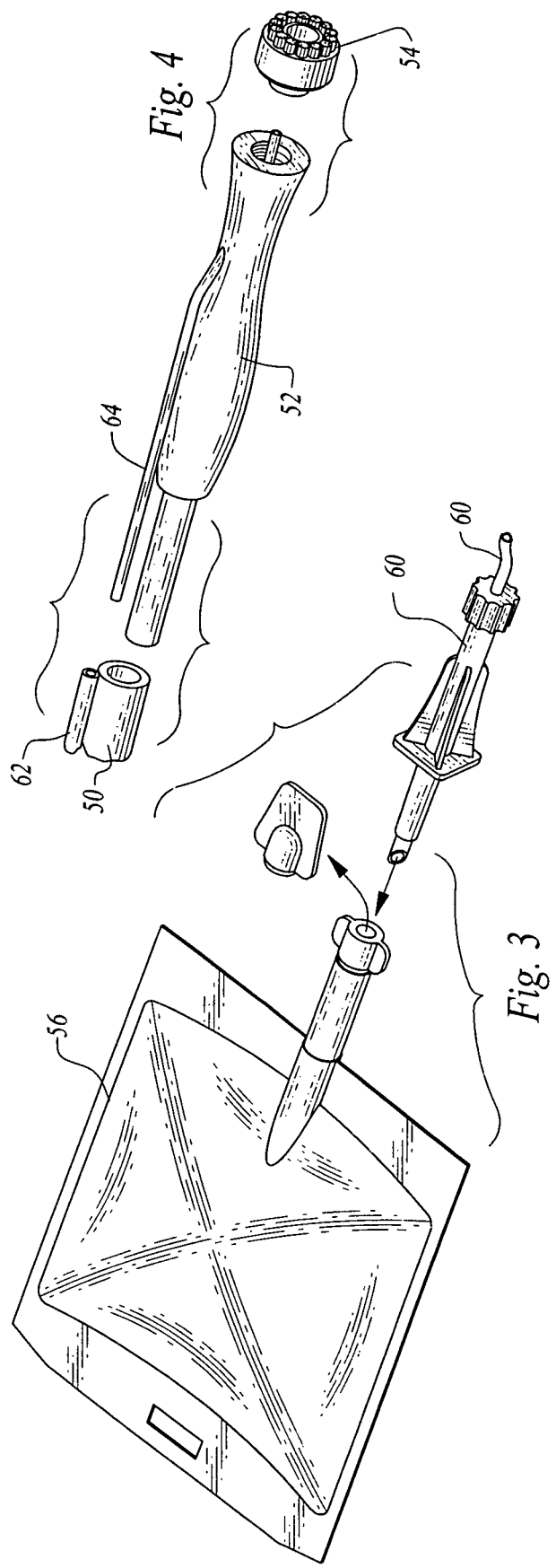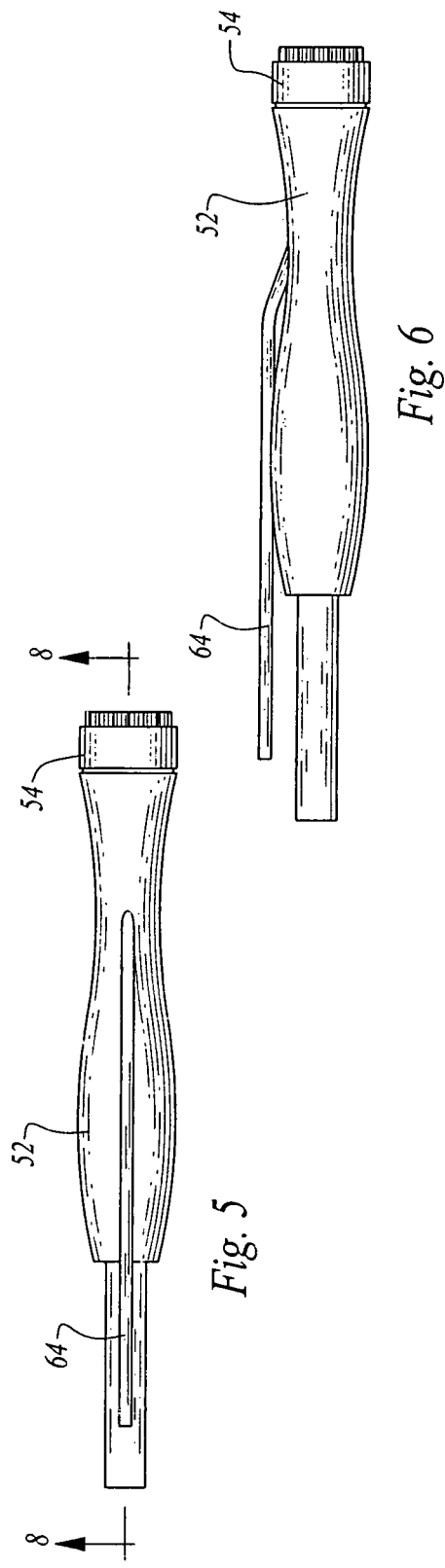

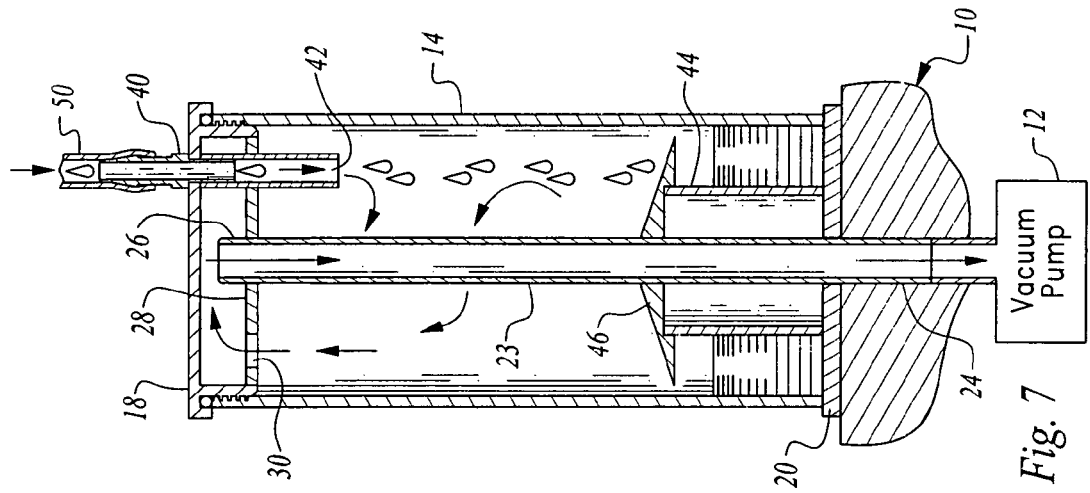
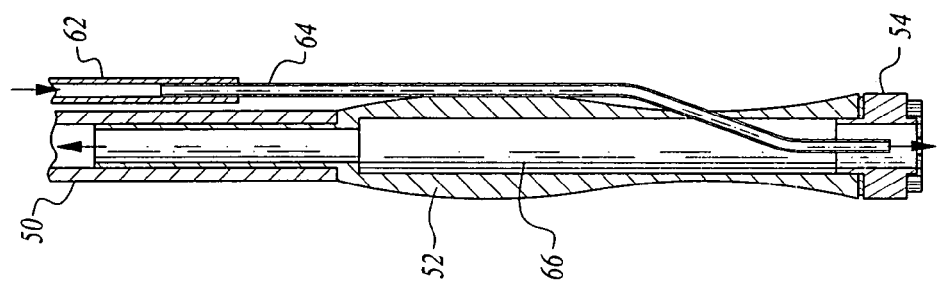
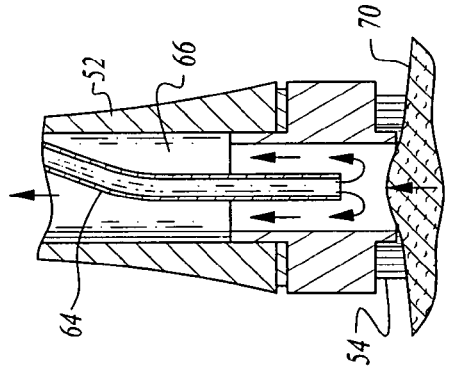
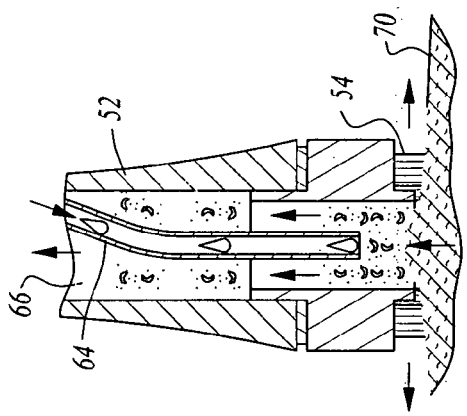
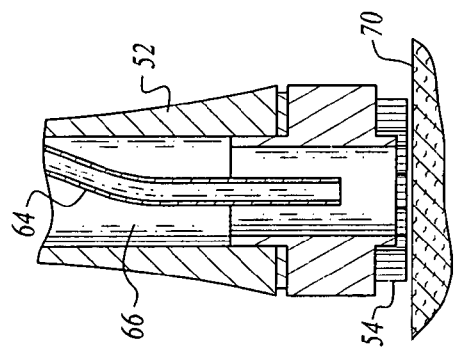
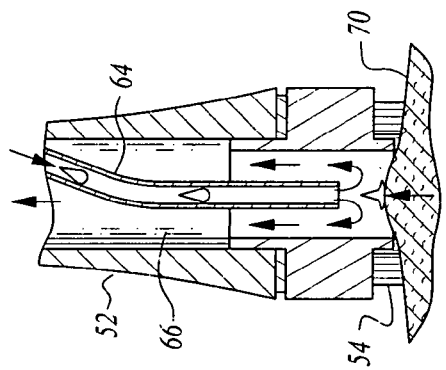

SKIN TREATMENT SYSTEM

This application is a continuation-in-part of U.S. patent application Ser. No. 11/172,698, filed Jun. 30, 2005.

TECHNICAL FIELD

This invention relates to apparatus for abrading skin to remove outer portions thereof and for delivering a liquid topical solution thereto.

BACKGROUND OF THE INVENTION

Dermabrasion, sometimes referred to as microdermabrasion, is a well known process for removing dead cells from the outermost layer of the skin, cleaning out blocked pores and enhancing skin tone. U.S. Pat. No. 6,241,739, discloses a treatment tool and tissue collection system for removing outer layers of skin to provide a revitalized, fresh skin surface, the objective being to remove dead and old skin cells without damaging the remaining skin surface and without the use of powdered abrasive material.

More particularly, U.S. Pat. No. 6,241,739 discloses a device for microabrasion comprising a hollow tube with an abrasive material permanently attached to a skin contacting end. The abrasive coated tip is moved over the skin surface while a vacuum is applied through the tube to the skin surface to remove cells abraded from the skin surface. The vacuum also causes the skin to be held in intimate contact with the abrasive tip during the treatment procedure. Specifically suggested as abrasion particles attached to the treatment tip are diamond grit, aluminum oxide, silicon carbide, silicon oxide, and various metal nitrates. Also suggested is the concept of machining or chemically treating the tip to provide a roughened surface which when moved across skin abrades the epidermis, dislodging cells from the surface. A method employing this technique is also disclosed in U.S. Pat. No. 6,241,739.

U.S. Pat. No. 6,500,183 matured from a continuation-in-part application based on the patent application resulting in above-described U.S. Pat. No. 6,241,739. U.S. Pat. No. 6,500,183 discloses a treatment tool and tissue collection system for removal of outer layers of skin to provide a revitalized, fresh skin surface, and a method of using same. The tool is an abrasive tipped tool mounted on the end or within the end of a hollow tube, the tube being connected to a source of vacuum. The vacuum aids in maintaining intimate contact between the abrasive tip and the skin during the treatment process and transports the removed tissue to a collection container. The abrasive surface within the tube is a motor driven abrasive pad. Contact between the pad and the abrasive disc is brought about or increased by application of a vacuum through the tube to the skin surface. Other prior art abrasion techniques are known, some of which can be traced back to ancient times wherein alabaster and pumice were utilized to remove blemishes and rough spots and to make the skin smooth and soft.

U.S. Pat. Nos. 2,712,823, 2,867,214, 2,881,763 and 2,921,585 disclose abrasive tipped devices or rotating brushes and cylinders coated with abrasive particles such as diamond dust to remove skin layers.

U.S. Pat. No. 5,800,446 describes a stick, fingertip or glove palm coated with an abrasive material which is rubbed over the skin surface to provide a polishing action. U.S. Pat. No. 3,964,212 discloses a pneumatic grinding machine for flat surfaces. U.S. Pat. No. 4,378,804 discloses a skin abrasion device which uses flowing water to rotate an abrasive brush and create a vacuum to remove loosened skin particles. The rotating brush is usually employed in conjunction with a liquid detergent or medicinal compound applied to the skin surface being scrubbed.

U.S. Pat. No. 5,012,797 shows the use of an ultrasonic surgical tool adapted to abrade soft tissue wherein use of the tool is accompanied by use of rinsing liquid such as an aqueous saline solution and suction means to withdraw the rinsing fluid as well as blood and tissue fragments upwardly into a pipe for disposal. U.S. Pat. No. 5,037,431 describes a hand-held surgical apparatus wherein a pressurized jet of a liquid, such as water or sterile saline, is employed to fragment diseased tissue and remove the liquid and fragmented tissue by vacuum.

It is also known to abrade the skin surface using powdered aluminum oxide or a liquid topical composition containing suspended aluminum oxide, as disclosed for example in U.S. Pat. No. 4,957,747. In the arrangement of U.S. Pat. No. 5,037,432 abrasive reducing substances are conveyed under pressure to the skin and a collection tube removes under suction both the reducing substances and the portions of tissue removed during the treatment. Somewhat similar arrangements, employing collection chambers, are disclosed in U.S. Pat. Nos. 5,100,412, 5,207,234 and 5,810,842.

U.S. Pat. No. 5,971,999 is related to an apparatus for microdermabrading by means of a jet of a mixture of air and reducing crystals, and an associated handle. The jet of reducing crystals is, in particular, a jet of corundum crystals.

U.S. Pat. No. 6,042,552 discloses a device for collecting fragments of walls of internal organs and U.S. Pat. No. 2,701,559 discloses apparatus for exfoliating and collecting diagnostic material from inner walls of hollow visera.

U.S. Pat. No. 6,641,591 discloses an instrument and technique for the removal of epidermal layers. The instrument abrades surface layers of the epidermis while at the same time causing rapid penetration of fluids into the skin. U.S. Patent Application Publication No. 2004/0143274 discloses a similar approach.

U.S. Pat. No. 6,695,583 discloses a microdermabrasion system and method of use wherein a vacuum head base defines a chamber. A smooth treatment tip has an opening open to the chamber. An abrasive member is in the chamber. One or more fluids are drawn into the chamber by a vacuum. The vacuum draws a portion of the skin into the chamber where it contacts the abrasive member and is contacted by the fluid(s).

U.S. Pat. Nos. 2,921,585, 5,207,234 and 6,423,078 show other dermabrasion approaches. U.S. Pat. Nos. 5,121,388, 4,646,482 and 5,035,089 relate to non-medical abrasion systems.

U.S. Patent Application Publication No. US2004/0010268 discloses dermabrasion/microdermabrasion apparatus including a hand piece. Negative and positive pressure is provided to the hand piece. A brush wheel and turbine in the hand piece are rotated by the air pressure and the rotating brush wheel is engaged with the user's skin.

DISCLOSURE OF INVENTION

The present invention relates to a unique combination of structural elements which cooperate in a unique manner to abrade skin, remove the abraded skin and provide for the application of a liquid topical solution to the skin under treatment. The apparatus includes a vacuum source, a container containing liquid topical solution and a hand-held applicator wand.

The hand-held applicator wand includes a skin abrading brush operatively associated with the vacuum source and with the container. The hand-held applicator wand is operable to substantially simultaneously engage and abrade the skin and to deliver liquid topical solution from the container to the skin at the skin abrading brush.

A receptacle is operatively connected to the hand-held applicator wand for receiving exfoliated skin particles produced by the skin abrading brush along with any excess liquid topical solution not absorbed by or retained on the skin at the location of the skin abrading brush.

The receptacle is of unique construction and comprises a collection canister operatively associated with the vacuum source. Vacuum applied to the collection canister by the vacuum source creates a fluid flow from the hand-held wand to the collection canister to entrain and deliver the exfoliated skin particles and excess liquid topical solution to the collection canister.

Other features, advantages and objects of the present invention will become apparent with reference to the following description and accompanying drawings.

BRIEF DESCRIPTION OF DRAWINGS

FIG. 3 is an exploded, perspective view illustrating a container in the form of an IV bag utilized in the apparatus for holding a liquid topical solution, the figure also illustrating an IV spike prior to insertion into the IV bag;

FIG. 4 is an exploded view illustrating a hand-held applicator wand incorporated in the apparatus prior to attachment of the wand to tubing/conduit structure;

FIG. 5 is a top, plan view of the hand-held applicator wand;

FIG. 6 is a side, elevational view of the hand-held applicator wand;

FIG. 7 is an enlarged, cross-sectional view of the collection canister in association with a vacuum pump and illustrating operation thereof to separate liquid and exfoliated skin particles from entraining air flow caused by the vacuum pump;

FIG. 8 is an enlarged, cross-sectional view taken along the line 8-8 of FIG. 6 and illustrating fluid flow in the hand-held applicator wand during operation; and FIGS. 9-12 are enlarged, cross-sectional views illustrating the distal end portion of the hand-held applicator wand, including the skin abrading brush thereof, during different stages of operation relative to a user's skin.

BEST MODE FOR CARRYING OUT THE INVENTION

Figure 2:
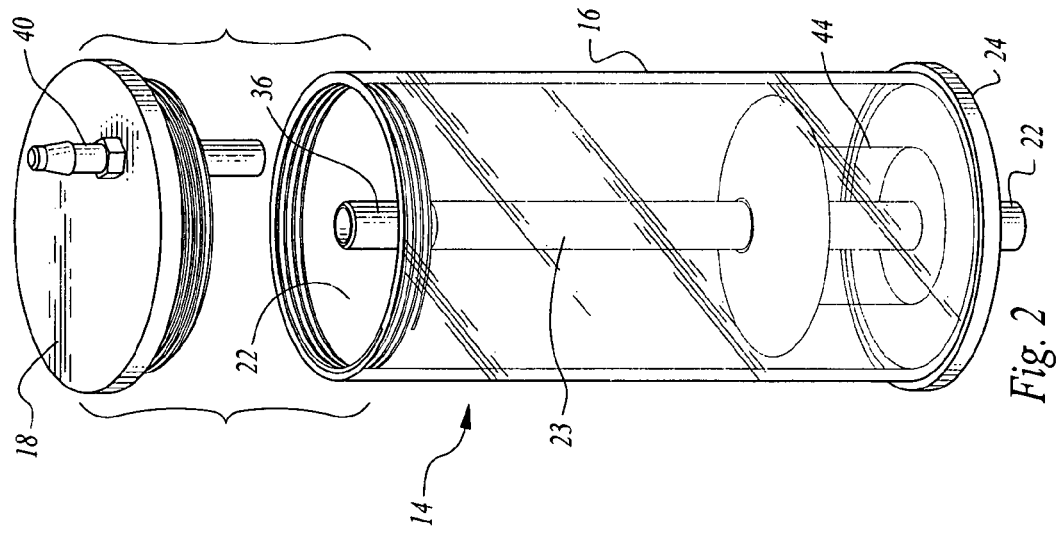
FIG. 2 is an exploded, perspective view illustrating the collection canister.
Figure 1:
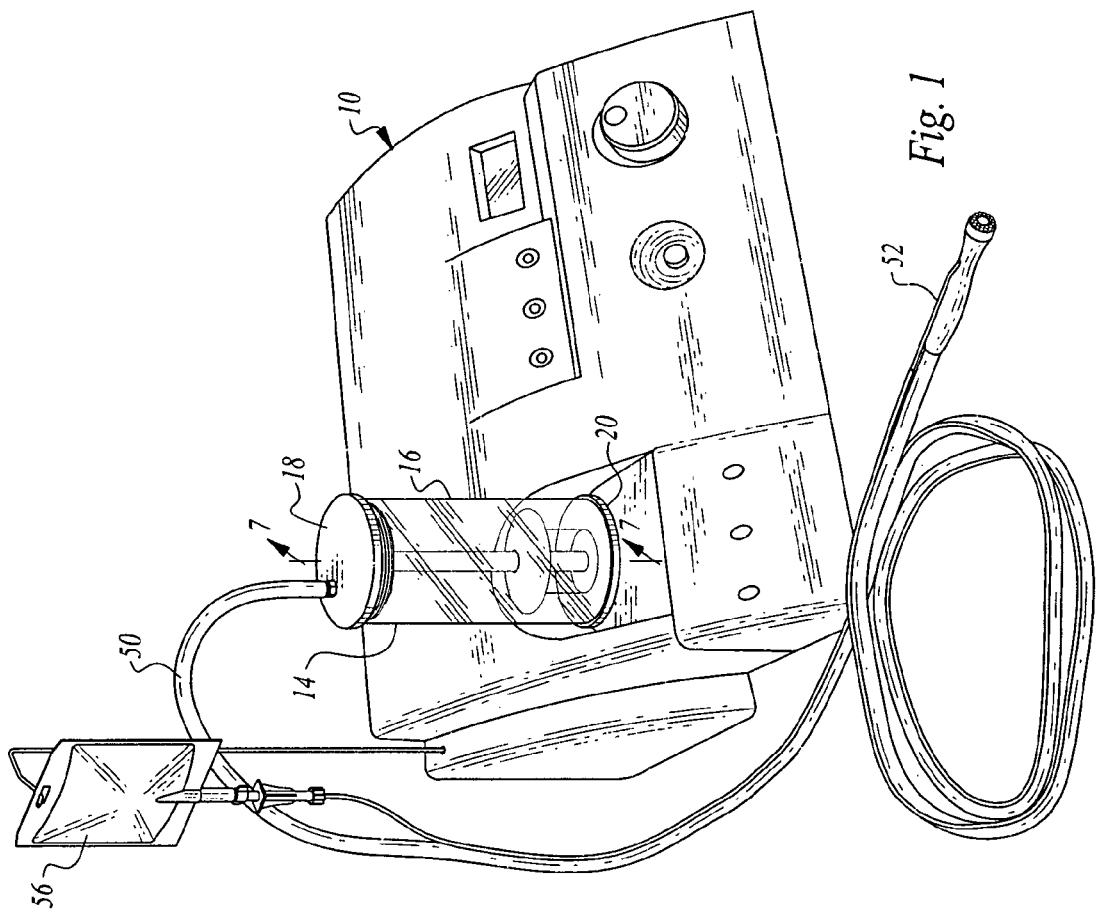
FIG. 1 is a perspective view of apparatus constructed in accordance with the teachings of the present invention and including a structural arrangement providing for simultaneous liquid topical solution delivery and exfoliation, the structure including a collection canister on a housing for receiving and collecting exfoliated skin particles and entrained liquid such as excess liquid topical solution and blood.

Referring now to the drawings, apparatus constructed in accordance with the teachings of the present invention is illustrated. The apparatus includes a housing 10 within which is disposed a vacuum pump 12 of any suitable type. The vacuum pump 12 is shown in block diagram format in FIG. 7. Suitable controls on the housing or console 10 are utilized to turn the vacuum pump on or off. Preferably, the vacuum applied by the vacuum pump may be varied by the operator.

Supported by housing 10 is a receptacle comprising a collection canister 14 operatively associated with the vacuum pump. Vacuum applied to the collection canister by the vacuum pump creates a fluid flow utilized to entrain and deliver exfoliated skin particles and liquid in a manner to be described in greater detail below. The collection canister is releasably connected to and selectively removable from the housing and is suitably of a disposable or one-time use nature. The collection canister includes a canister wall 16, a canister top 18 which is suitably removable as shown in FIG. 3, and a canister bottom 20 positioned on the housing, as shown.

The collection canister includes trap structure for trapping exfoliated skin particles, excess liquid topical solution and other liquids involved in the treatment process, possibly including blood.

The collection canister defines a canister interior 22 within which the exfoliated skin particles and liquids are collected. The collection canister has a canister outlet and a canister inlet, the canister inlet and the canister outlet being spaced from one another and in fluid-flow communication with the canister interior. More particularly, the canister outlet is an outlet tube 23 having an open lower end 24, the outlet tube 23 extending downwardly from canister bottom 20 into a passageway in the housing communicating with the vacuum pump 12. The outlet tube 23 has an open outlet tube upper end 26 which terminates within the canister interior below the canister top 18. A partition wall 28 is spaced from and disposed below the canister top. The open outlet tube upper end 26 is disposed above the partition wall 28. The partition wall defines a partition wall opening 30. In the arrangement illustrated, the partition wall is integral with canister top 18, although it need not be.

The collection canister inlet is in the form of an inlet tube 40 projecting into the canister interior through the canister top and through the partition wall 28. The inlet tube is open at both the upper and lower ends thereof, the open inlet tube lower end 42 located within the collection canister interior below the partition wall 28.

A cylindrically-shaped spacer wall 44 extends upwardly from the canister bottom 20 and surrounds the outlet tube 23. The spacer wall is spaced inwardly from the canister wall 16 and defines therewith an annular space for receiving exfoliated skin particles and liquid. A deflector shield 46 is disposed over the spacer wall to deflect the exfoliated skin particles and liquid into the annular space.

Flexible tubing 50 is attached to the upper end of inlet tube 40, the flexible tubing 50 leading to a hand-held applicator wand 52 including a detachable skin abrading brush 54 at the distal end thereof. The brush may be one of a series of interchangeable brushes having different stiffnesses or other physical characteristics employed to treat skin.

The apparatus disclosed and claimed herein has the capability of simultaneously abrading the skin and delivering liquid topical solution to the skin at the skin abrading brush 54. In the arrangement illustrated, the container is in the form of a small IV bag 56 depending from an IV bag support 58 extending upwardly from the housing. The liquid topical solution may be of many types, for example, solutions employed for medical, cosmetic or cleansing purposes.

FIG. 3 shows a conventional IV bag spike 60 being inserted into the neck of the IV bag 56. A flexible conduit portion 62 of relatively small diameter leads from the IV bag spike and connects with a rigid conduit portion 64 affixed to the hand-held applicator wand and terminating within the interior passageway 66 of the wand which is in fluid-flow communication with flexible tubing 50. The distal end of rigid conduit portion 64 terminates within the interior passageway at a location spaced from the skin abrading brush 54.

FIG. 9 shows the skin abrading brush 54 prior to engagement with the skin 70 of a user or patient. FIG. 10 shows the brush in engagement with the skin, the vacuum produced in interior passageway 66 drawing a portion of the skin upwardly within the confines of the brush as shown. This induces an ambient air flow through the brush which entrains exfoliated skin particles produced by movement of the brush relative to the skin. FIG. 12 shows two horizontal arrows which illustrate back and forth movement of the brush relative to the skin and also entrainment of exfoliated skin particles.

The vacuum produced within the interior passageway 66 also results in a vacuum at the lower end of rigid conduit portion 64 which draws liquid topical solution from the IV bag 56 and out the lower exit end of rigid conduit portion 64. Due to the close proximity between the rigid conduit portion and the raised skin portion, the liquid topical solution will impact the skin portion as shown in FIG. 11. The exfoliated skin particles and excess liquid topical solution, as well as any blood produced will be drawn through flexible tubing 50 to inlet tube 40.

FIG. 7 illustrates the operation of the trap structure described above utilized to trap the exfoliated skin particles and liquid associated therewith. The skin particles and liquid moves in a downward direction after exiting the inlet tube 40, impacts deflector shield 46 and is collected in the annular space between canister wall 16 and spacer wall 44. Air flow after separation of the skin particles and liquid therefrom will, as illustrated by arrows in FIG. 7, proceed upwardly through the upper end of the canister interior, through partition wall opening 30 into the space between the partition wall and the canister top, and thence downwardly through the outlet tube 23.

The invention claimed is:

1. Apparatus for abrading skin simultaneously delivering a liquid topical solution to the skin, said apparatus comprising in combination:
   a vacuum source;
   a container containing liquid topical solution;
   a hand-held applicator wand including a skin abrading brush operatively associated with said vacuum source and with said container, said hand-held applicator wand operable to substantially simultaneously engage and abrade the skin and to deliver liquid topical solution from said container to said skin at said skin abrading brush;
   a receptacle operatively connected to said hand-held applicator wand for receiving exfoliated skin particles produced by said skin abrading brush along with any excess liquid topical solution not absorbed by or retained on the skin at the location of said skin abrading brush, said receptacle comprising a collection canister operatively associated with said vacuum source, vacuum applied to said collection canister by said vacuum source creating a fluid flow from said hand-held wand to said collection canister to entrain and deliver said exfoliated skin particles and excess liquid topical solution to said collection canister;
   a housing, said collection canister including a canister wall and releasably connected to and selectively removable from said housing, said collection canister defining a canister interior, a canister outlet, and a canister inlet, said canister inlet and said canister outlet being spaced from one another and in fluid-flow communication with said canister interior, said collection canister including trap structure for trapping said exfoliated skin particles and excess liquid topical solution and retaining said exfoliated skin particles and excess liquid topical solution in said canister interior between said canister outlet and said canister inlet, and said collection canister additionally including a canister top and a canister bottom, said trap structure including an upstanding outlet tube having an open outlet tube lower end comprising said canister outlet and an open outlet tube upper end terminating within the canister interior below said canister top, said trap structure additionally including a downwardly extending inlet tube projecting into said canister interior through said canister to and having an open inlet tube lower end terminating below said open outlet tube upper end; and
   flexible conduit interconnecting said inlet tube to said hand-held applicator wand, said trap structure additionally comprising a partition wall spaced from and disposed below said canister top, said open outlet tube upper end being disposed above said partition wall and said open inlet tube lower end terminating below said partition wall, said partition wall defining a partition wall opening allowing a vacuum induced air flow from the inlet tube, through said canister interior below said partition wall into the space between the canister top and partition wall, and thence downwardly through said outlet tube after entrapping said exfoliated skin particles and excess liquid topical solution within said container interior.

2. The apparatus according to claim 1 wherein said trap structure additionally comprises a spacer wall extending upwardly from said canister bottom, spaced inwardly from said canister wall and defining therewith an annular space for receiving said exfoliated skin particles and excess liquid topical solution and a deflector shield over said spacer wall for deflecting said exfoliated skin particles and excess liquid topical solution into said annular space.

3. The apparatus according to claim 1 wherein said hand-held applicator wand defines an interior passageway leading from said skin abrading brush, ambient air flow induced by said vacuum source flowing through and past said skin abrading brush through said interior passageway and to said receptacle, said hand-held applicator wand additionally including a conduit terminating within said interior passageway at a location spaced from said skin abrading brush, said conduit leading to said container and operable to deliver said liquid topical solution to said skin at said skin abrading brush responsive to formation of a vacuum in said interior passageway by said vacuum source.

* * * * *